(12) United States Patent
Song et al.

(10) Patent No.: US 8,969,630 B2
(45) Date of Patent: *Mar. 3, 2015

(54) METHOD FOR PREPARING CHLOROHYDRINS AND METHOD FOR PREPARING EPICHLOROHYDRIN USING CHLOROHYDRINS PREPARED THEREBY

(75) Inventors: Won Seob Song, Ulsan (KR); Sung Yul Woo, Ulsan (KR); Boo Weon Song, Ulsan (KR); Seong Han Park, Ulsan (KR); Myoung Suk Kwon, Ulsan (KR)

(73) Assignee: Samsung Fine Chemicals Co., Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/805,750

(22) PCT Filed: Jun. 8, 2011

(86) PCT No.: PCT/KR2011/004168
§ 371 (c)(1),
(2), (4) Date: Dec. 20, 2012

(87) PCT Pub. No.: WO2012/002648
PCT Pub. Date: Jan. 5, 2012

(65) Prior Publication Data
US 2013/0096327 A1  Apr. 18, 2013

(30) Foreign Application Priority Data
Jun. 30, 2010 (KR) ........................ 10-2010-0063157

(51) Int. Cl.
*C07C 31/34* (2006.01)
*C07D 301/02* (2006.01)
(Continued)

(52) U.S. Cl.
CPC .............. *C07C 29/62* (2013.01); *C07D 303/08* (2013.01)

USPC .................................... 568/844; 549/518

(58) Field of Classification Search
CPC ........ C07C 29/62; C07C 29/80; C07C 31/36; C07D 303/08; C07D 301/26
USPC ...................... 549/518, 514; 568/844
See application file for complete search history.

(56) References Cited

U.S. PATENT DOCUMENTS

2013/0102799 A1* 4/2013 Song et al. ................... 549/514

FOREIGN PATENT DOCUMENTS

| CN | 101031532 A | 9/2007 |
|----|-------------|--------|
| CN | 101208323 A | 6/2008 |

(Continued)

OTHER PUBLICATIONS

Written Opinion with English Translation for International Application No. PCT/KR2011/004168 dated Feb. 16, 2012.
(Continued)

*Primary Examiner* — T. Victor Oh
(74) *Attorney, Agent, or Firm* — Cantor Colburn LLP

(57) ABSTRACT

A method of preparing chlorohydrins and a method of preparing epichlorohydrin by using chlorohydrins prepared using the method are provided. The method of preparing chlorohydrins by reacting polyhydroxy aliphatic hydrocarbon with a chlorination agent in the presence of a catalyst includes at least one combination of a series of unit operations including a first reaction step, a water removal step, and a second reaction step, in that respective order, wherein the method further includes purifying chlorohydrins from a reaction mixture discharged from a final reaction step of the plurality of reaction steps. The method of preparing epichlorohydrin includes reacting chlorohydrins prepared using the method of preparing chlorohydrins, with an alkaline agent.

29 Claims, 1 Drawing Sheet

(51) Int. Cl.
 *C07C 29/62* (2006.01)
 *C07D 303/08* (2006.01)

(56) References Cited

FOREIGN PATENT DOCUMENTS

| CN | 101541418 A | 9/2009 |
|---|---|---|
| CN | 101636370 A | 1/2010 |
| KR | 1020070034599 A | 3/2007 |
| KR | 1020080037613 A | 4/2008 |
| KR | 1020090032429 A | 4/2009 |
| WO | WO2006/100320 * | 9/2006 |
| WO | WO2009/041766 * | 4/2009 |
| WO | 2009066327 A1 | 5/2009 |

OTHER PUBLICATIONS

International Search Report with English Translation for International Application No. PCT/KR2011/004168 dated Feb. 16, 2012.
Chinese Office Action with English Translation for Application No. 201180032091.1 dated Apr. 30, 2014.

* cited by examiner

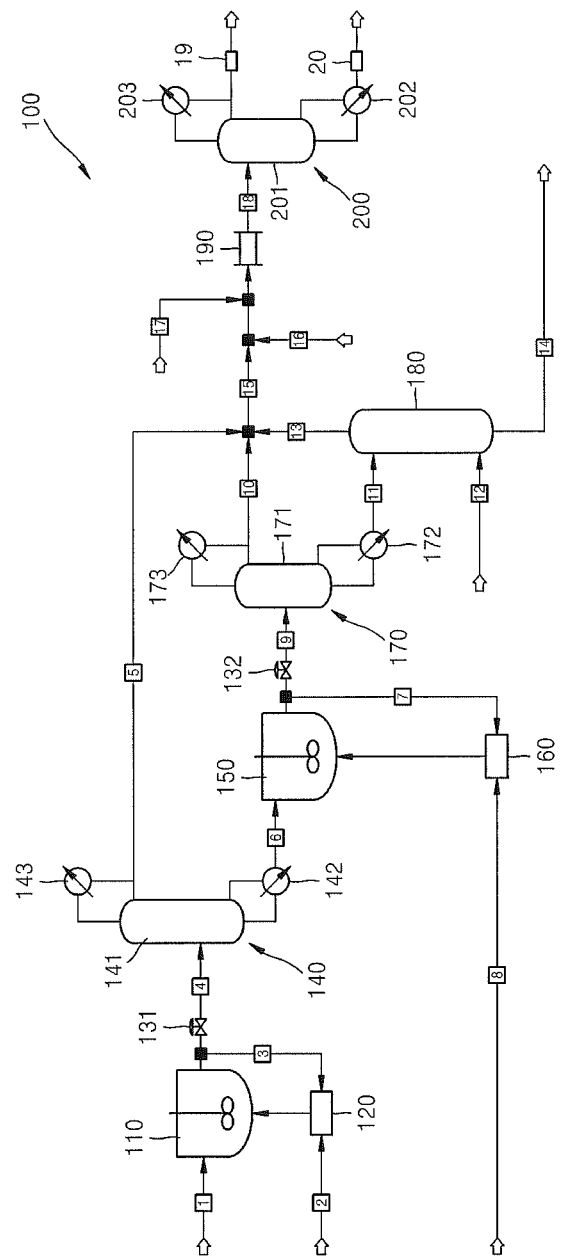

METHOD FOR PREPARING CHLOROHYDRINS AND METHOD FOR PREPARING EPICHLOROHYDRIN USING CHLOROHYDRINS PREPARED THEREBY

TECHNICAL FIELD

One or more embodiments of the present invention relate to a method of preparing chlorohydrins and a method of preparing epichlorohydrin by using chlorohydrins prepared using the method. More particularly, one or more embodiments of the present invention relate to a method of preparing chlorohydrins by reacting polyhydroxy aliphatic hydrocarbon with a chlorination agent in the presence of a catalyst, the method including a plurality of reaction steps and a water removal step performed between the plurality of reaction steps, wherein the method further includes purifying chlorohydrins from a reaction mixture discharged from a final reaction step of the plurality of reaction steps, and a method of preparing epichlorohydrin which includes reacting chlorohydrins prepared using the method with an alkaline agent.

BACKGROUND ART

Recently, bio-diesels have been competitively developed and produced worldwide, and have also been domestically manufactured and commercially used as an additive to petro-diesel.

During the production of bio-diesel, a large amount of glycerol, corresponding to about 10% of the amount of the produced bio-diesel, is generated. However, supply of glycerol is greater than demand therefor, which leads to a continuous decrease in its value. Thus, it is economically advantageous to convert glycerol into chlorohydrins such as dichloropropanol which is a higher-value added product than glycerol.

Meanwhile, chlorohydrins such as dichloropropanol are used as a raw material for preparing epichlorohydrin. Most chlorohydrins which are currently supplied to markets are manufactured from propylene. Particularly, a method of preparing chlorohydrins includes two steps: preparing allyl chloride by high temperature chlorination of propylene and forming the chlorohydrins by reacting the allyl chloride with a chlorination agent using an excess amount of industrial water. However, the method of preparing chlorohydrins using propylene has problems in terms of instability of propylene supply and demand caused by increased price of propylene, generation of a large amount of waste water and other wastes, excessive initial investment costs due to the two-step manufacturing process, and the resulting difficulty in newly constructing/modifying a manufacturing apparatus.

Accordingly, a single-stage process of directly preparing chlorohydrins by reacting a polyhydroxy aliphatic hydrocarbon such as glycerol, which is a by-product of bio-diesels, with a chlorination agent in the presence of a catalyst is more economical. Such a single-stage process using polyhydroxy aliphatic hydrocarbon such as glycerol as a raw material is advantageous in that costs of raw materials can be reduced by using inexpensive polyhydroxy aliphatic hydrocarbon, the amount of waste water and other wastes can be dramatically reduced since industrial water is not required for the process, and thus the process is environmentally friendly, and initial investment costs related to the process and environment can be reduced.

However, when the method of preparing a chlorohydrin is used, water is produced as a by-product and the produced water inhibits chlorination of polyhydroxy aliphatic hydrocarbon such as glycerol. Thus, as the reaction proceeds, the reaction rate gradually decreases, and the selectivity of chlorohydrins is reduced.

DETAILED DESCRIPTION OF THE INVENTION

Technical Problem

The present invention provides a method of preparing chlorohydrins by reacting polyhydroxy aliphatic hydrocarbon with a chlorination agent in the presence of a catalyst, the method including a plurality of reaction steps and a water removal step performed between the plurality of reaction steps, wherein the method further includes purifying chlorohydrins from a reaction mixture discharged from a final reaction step of the plurality of reaction steps.

The present invention also provides a method of preparing epichlorohydrin which includes reacting chlorohydrins prepared using the method with an alkaline agent.

Technical Solution

According to an aspect of the present invention, there is provided a method of preparing chlorohydrins by reacting polyhydroxy aliphatic hydrocarbon with a chlorination agent in the presence of a catalyst, the method including at least one combination of a series of unit operations including a plurality of reaction steps and a water removal step in the following stated order: a first reaction step of reacting the polyhydroxy aliphatic hydrocarbon with the chlorination agent; a water removal step of removing water as a by-product from a reaction mixture discharged from the first reaction step; and a second reaction step of reacting at least one constituent of the dehydrated reaction mixture with at least one of the chlorination agent and an additional chlorination agent, wherein the method further includes purifying a reaction mixture discharged from a final reaction step of the plurality of reaction steps to obtain a concentrate of chlorohydrins.

The method may further include mixing at least a portion of a reaction mixture discharged from at least one reaction steps from among the plurality of reaction steps, with an additional chlorination agent and then recirculating the resultant mixture to the reaction step from which the reaction mixture was discharged.

According to another aspect of the present invention, there is provided a method of preparing chlorohydrins, the method including: introducing polyhydroxy aliphatic hydrocarbon, a catalyst, and a chlorination agent into a first reactor maintained at a temperature of 50 to 200° C.; discharging from the first reactor an effluent of the first reactor including water as a by-product; introducing at least a portion of the effluent of the first reactor into a water removal device; introducing the effluent of the first reactor from which water is removed, and an additional chlorination agent into a second reactor maintained at a temperature of 80 to 200° C.; and introducing at least a portion of an effluent of the second reactor into a device for purifying chlorohydrins to obtain a concentrate of chlorohydrins.

The method may further include at least one of a step of introducing at least a portion of the effluent of the first reactor with an additional chlorination agent into a first mixer, mixing them together, and recirculating the resulting mixture to the first reactor; and a step of introducing at least a portion of the effluent of the second reactor with an additional chlorination agent into a second mixer, mixing them together, and recirculating the resulting mixture to the second reactor.

The polyhydroxy aliphatic hydrocarbon may be a $C_2$-$C_{20}$ compound having at least two hydroxyl groups bonded to different carbon atoms.

The polyhydroxy aliphatic hydrocarbon may include at least one compound selected from the group consisting of 1,2-ethanediol, 1,2-propanediol, 1,3-propanediol, 3-chloro-1,2-propanediol, 2-chloro-1,3-propanediol, glycerol, 1,2,4-butanetriol, 1,4-butanediol, and esters of these compounds.

Chlorohydrins of the concentrate of chlorohydrins may be compounds having at least one hydroxyl group and at least one chlorine atom which are bonded to different carbon atoms.

The chlorohydrins may include at least one compound selected from the group consisting of 3-chloro-1,2-propanediol, 2-chloro-1,3-propanediol, 1,3-dichloropropane-2-ol, and 2,3-dichloropropane-1-ol.

The catalyst may include at least one selected from the group consisting of an organic acid catalyst, a carboxylic acid-based catalyst, a nitrile-based catalyst, and a solid catalyst.

A reaction product of the catalyst and the polyhydroxy aliphatic hydrocarbon may be produced as an intermediate product in the first reactor, and the intermediate product may act as a catalyst in a chlorination reaction of the polyhydroxy aliphatic hydrocarbon.

The polyhydroxy aliphatic hydrocarbon may include glycerol, the catalyst may include acetic acid, and the intermediate product may include glycerol acetates.

The chlorination agent and/or the additional chlorination agent may include a hydrogen chloride gas or an aqueous hydrochloric acid solution.

The effluent of the first reactor introduced into the water removal device may be discharged when a conversion rate of the polyhydroxy aliphatic hydrocarbon is from 30 to 100% and a yield of chlorohydrins is 30 to 95%, in the first reactor.

The effluent of the first reactor introduced into the water removal device may include 0 to 90 parts by weight of the polyhydroxy aliphatic hydrocarbon; 5 to 95 parts by weight of the chlorohydrins; and 5 to 12 parts by weight of the intermediate product.

The effluent of the first reactor introduced into the water removal device may include 10 to 25 parts by weight of the total of the chlorination agent and the additional chlorination agent and 75 to 90 parts by weight of water.

The device for purifying chlorohydrins may include a distillation device.

The device for purifying chlorohydrins may further include a stripping device at a rear end of the distillation device.

A retention time of the reactor contents in the first reactor may be from 20 minutes to 1 hour, and a retention time of the reactor contents in the second reactor may be from 1 to 3 hours.

The water removal device may perates by performing distillation using a difference between boiling points of constituents of the effluent of the first reactor.

The first and second reactors may be maintained at an atmospheric pressure or higher, and the water removal device may be maintained at an atmospheric pressure or lower.

The first and second reactors may be maintained at 1 to 20 atm, and the water removal device may be maintained at 10 to 760 mmHg.

The water removal device may include a vacuum distillation column having a theoretical plate number of 2 to 50.

The effluent of the first reactor may be decompressed in a decompression device and then introduced into the water removal device.

The decompression device may include a decompression valve.

The first and second reactors may be each independently a continuous stirred tank reactor, a batch reactor, a semi-batch reactor, or a plug flow reactor.

The effluent of the first reactor introduced into the water removal device may be separated into a water-rich layer and a water-deficient layer.

A portion of the effluent of the second reactor which is introduced into the device for purifying chlorohydrins may include 0 to 10 parts by weight of the polyhydroxy aliphatic hydrocarbon, 80 to 98 parts by weight of the chlorohydrins, 0 to 10 parts by weight of the total of the chlorination agent and the additional chlorination agent, and 1 to 20 parts by weight of water.

According to another aspect of the present invention, there is provided a method of preparing epichlorohydrin, the method including contacting a composition of chlorohydrins including chlorohydrins prepared using the method described above, with an alkaline agent at 20 to 100° C., wherein the composition of chlorohydrins includes 0 to 5 parts by weight of the polyhydroxy aliphatic hydrocarbon, 10 to 40 parts by weight of the chlorohydrins, 0 to 5 parts by weight of the total of the chlorination agent and the additional chlorination agent, and 50 to 90 parts by weight of water.

The composition of chlorohydrins may further include a catalyst, wherein the catalyst reacts with the alkaline agent to form an alkali metal salt.

Advantageous Effects

According to an embodiment of the present invention, a method of preparing chlorohydrins provides an improved selectivity of chlorohydrins.

According to another embodiment of the present invention, a method of preparing epichlorohydrin includes reacting chlorohydrins prepared using the method with an alkaline agent.

DESCRIPTION OF THE DRAWINGS

The above and other features and advantages of the present invention will become more apparent by describing in detail exemplary embodiments thereof with reference to the attached drawing in which:

FIG. 1 is a process flow diagram illustrating a method of preparing chlorohydrins and a method of preparing epichlorohydrin by using chlorohydrins prepared using the method, according to an embodiment.

BEST MODE

Hereinafter, a method of preparing chlorohydrins and a method of preparing epichlorohydrin, according to embodiments of the present invention, will be described in detail with reference to the accompanying drawing. In the specification, the method of preparing chlorohydrins may be intended to mean a method of preparing a composition of chlorohydrins, in some cases.

The method of preparing chlorohydrins according to the present embodiment includes reacting polyhydroxy aliphatic hydrocarbon with a chlorination agent in the presence of a catalyst.

The method of preparing chlorohydrins includes at least one combination of a series of unit operations including a plurality of reaction steps and a water removal step in the following stated order: a first reaction step of reacting polyhydroxy aliphatic hydrocarbon with a chlorination agent; a water removal step of removing water as a by-product from a reaction mixture discharged from the first reaction step; and a second reaction step of reacting at least one constituent of the reaction mixture from which water is removed in the water removal step, with at least one of the chlorination agent and an additional chlorination agent. In addition, in the water removal step, a chlorination agent is not additionally added.

In addition, the method of preparing chlorohydrins may further include purifying a reaction mixture discharged from a final reaction step of the plurality of reaction steps to obtain a concentrate of chlorohydrins.

Hereinafter, the method of preparing chlorohydrins will be described in detail with reference to FIG. 1.

As used herein, the term "chlorohydrins" means chlorohydrin, an ester of chlorohydrin, or a mixture thereof.

The chlorohydrins may be compounds having at least one hydroxyl group and at least one chlorine atom which are bonded to different carbon atoms. For example, the chlorohydrins may include at least one compound selected from the group consisting of 3-chloro-1,2-propanediol, 2-chloro-1,3-propanediol, 1,3-dichloropropane-2-ol, and 2,3-dichloropropane-1-ol. In the present specification, 3-chloro-1,2-propanediol and 2-chloro-1,3-propanediol are collectively referred to as "monochloropropanediol," and 1,3-dichloropropane-2-ol and 2,3-dichloropropane-1-ol are collectively referred to as "dichloropropanol."

In the method of preparing chlorohydrins, 1,3-dichloropropane-2-ol is predominantly produced, and particularly, is suitable for use as a reactant to prepare epichlorohydrin.

Referring to FIG. 1, the polyhydroxy aliphatic hydrocarbon and the catalyst are introduced into a first reactor 110 via a line 1. In addition, the chlorination agent is introduced into the first reactor 110 via a line 2 and/or other paths.

The polyhydroxy aliphatic hydrocarbon may be a $C_2$-$C_{20}$ compound having at least two hydroxyl groups bonded to different carbon atoms. The polyhydroxy aliphatic hydrocarbon may include at least one compound selected from the group consisting of 1,2-ethanediol, 1,2-propanediol, 1,3-propanediol, 3-chloro-1,2-propanediol, 2-chloro-1,3-propanediol, glycerol, 1,2,4-butanetriol, 1,4-butanediol, and esters of these compounds.

The catalyst may be an organic acid catalyst, a carboxylic acid-based catalyst, a nitrile-based catalyst, a solid catalyst, or a mixture of at least two thereof.

The organic acid catalyst may include, for example, at least one compound selected from the group consisting of monocarboxylic acid, dicarboxylic acid, polycarboxylic acid, malonic acid, levulinic acid, citric acid, succinic acid, propionic acid, and derivatives of these organic acids.

The carboxylic acid-based catalyst may include, for example, at least one compound selected from the group consisting of monocarboxylic acid ester, polycarboxylic acid ester, monocarboxylic acid anhydrides, polycarboxylic acid anhydrides, monocarboxylic acid chlorides, polycarboxylic acid chlorides, monocarboxylic acid salts, polycarboxylic acid salts, and derivatives of these carboxylic acid based compounds.

The nitrile-based catalyst may include, for example, at least one compound selected from the group consisting of acetonitrile, propionitrile, acrylonitrile, valeronitrile, isobutyronitrile, hydroxyacetonitrile, chloroacetonitrile, succinonitrile, glutaronitrile, adiponitrile, and phenylacetonitrile.

The solid catalyst may include, for example, at least one compound selected from the group consisting of an inorganic oxide, an inorganic halide, a strong-acidic organic compound, and mixtures of at least two of these.

The inorganic oxide may include at least one compound selected from the group consisting of a metal oxide, a composite oxide, oxy acid, and an oxyacid salt. The metal oxide may be, for example, $SiO_2$, $Al_2O_3$, $TiO_2$, $Fe_2O_3$, $ZrO_2$, $SnO_2$, $CeO_2$, $Ga_2O_3$, or $La_2O_3$. The composite oxide may be, for example, $SiO_2$—$Al_2O_3$, $SiO_2$—$TiO_2$, $TiO_2$—$ZrO_2$, $SiO_2$—$ZrO_2$, $MoO_3$—$ZrO_2$, zeolite, a heteropoly acid (i.e., a poly acid including P, Mo, V, W, Si or the like), or a heteropoly acid salt. Examples of the oxy acid and oxy acid salt include $BPO_4$, $AlPO_4$, polyphosphoric acid, acidic phosphate, $H_3BO_3$, acidic borate, and niobic acid.

The inorganic halide may be a metal halide such as a metal fluoride, a metal chloride, a metal bromide, or a metal iodide of a Group 3A element such as scandium, yttrium, lanthanum, or actinium; a Group 4A element such as titanium, zirconium, or hafnium; a Group 5A element such as vanadium, niobium, or tantalum; a Group 8 element such as iron, cobalt, nickel, palladium, or platinum; a Group 2B element such as zinc; a Group 3B element such as aluminum or gallium; or a Group 4B element such as germanium or tin.

The strong acidic organic compound may be, for example, an organic sulfonic acid compound such as a sulfonate group-containing ion-exchange resin or a condensed carbon ring-containing sulfonic acid compound.

The amount of the catalyst introduced may be from 1 to 10 parts by weight based on 100 parts by weight of the polyhydroxy aliphatic hydrocarbon. When the amount of the catalyst introduced is within this range, a reaction rate may be satisfactorily improved with an appropriate amount of the catalyst.

In the method of preparing chlorohydrins, the first reactor 110 may be maintained at a temperature from 50 to 200° C. When the temperature of the first reactor 110 is within this range, a high reaction rate may be obtained by the application of an appropriate level of energy. In addition, the first reactor 110 may be maintained at an atmospheric pressure or higher, for example, at 1 to 20 atm. When the pressure of the first reactor 110 is within this range, relatively high reaction activity may be obtained. In this case, even though the pressure of the first reactor 110 is greater than 20 atm, an effect of an increase in reaction activity according to the increase in pressure is not significant. In addition, the first reactor 110 may be a continuous stirred tank reactor (CSTR), but is not limited thereto. For example, the first reactor 110 may be a batch reactor, a semi-batch reactor, a plug flow reactor. In the first reactor 110, chlorohydrins as a main product and a reaction product of the catalyst and the polyhydroxy aliphatic hydrocarbon, as an intermediate product, are produced. The intermediate product may act as a catalyst in the chlorination reaction of the polyhydroxy aliphatic hydrocarbon (e.g., a reaction for producing chlorohydrins which occurs in the first reactor 110 and/or a second reactor 150). For example, when the polyhydroxy aliphatic hydrocarbon includes glycerol and the catalyst includes acetic acid, the intermediate product may include glycerol acetates (or glycerine acetates). As used herein, the term "glycerol acetates" indicates a substituted or unsubstituted glycerol monoacetate, a substituted or unsubstituted glycerol diacetate, a substituted or unsubstituted glycerol triacetate, or a mixture of these compounds. In addition, the term "substituted" as used herein means that a hydrogen atom of the compound described above is substituted with a halogen group, a hydroxyl group, an alkyl group, an alkoxy group, an amine group, or a combination thereof. In addition, a retention time of the reactor contents in the first reactor 110 may be from 20 minutes to 1 hour. When the retention time of the reactor contents in the first reactor 110 is within this range, a high conversion rate of the polyhydroxy aliphatic hydrocarbon may be obtained within an appropriate time.

The chlorination agent may include a hydrogen chloride gas or an aqueous hydrochloric acid solution.

An example of the reaction occurring in the first reactor 110 is a chlorination reaction of the polyhydroxy aliphatic hydrocarbon (e.g., glycerol) which is represented by Reaction Scheme 1 below:

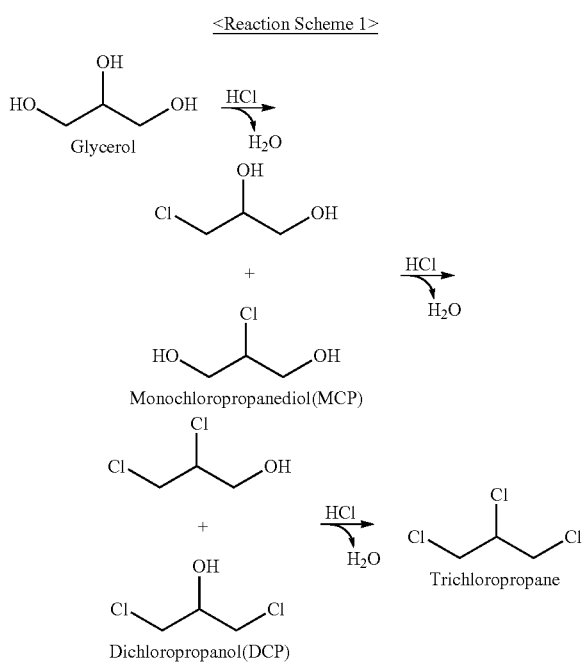

<Reaction Scheme 1>

In the above reaction, the conversion rate of glycerol, the yield of monochloropropanediol (MCP), the yield of dichloropropanol (DCP), the selectivity of MCP, and the selectivity of DCP may be calculated respectively by Equations 1 through 5 below:

Conversion rate of glycerol(%)=(number of moles of glycerol reacted)/(number of moles of glycerol introduced)×100     [Equation 1]

Yield of MCP(%)=(number of moles of MCP generated)/(number of moles of glycerol introduced)×100     [Equation 2]

Yield of DCP(%)=(number of moles of DCP generated)/(number of moles of glycerol introduced)×100     [Equation 3]

Selectivity of MCP=(number of moles of MCP generated)/(total number of moles of reaction products)×100     [Equation 4]

Selectivity of DCP=(number of moles of DCP generated)/(total number of moles of reaction products)×100.     [Equation 5]

After the retention time elapses, an effluent of the first reactor 110 is discharged from the first reactor 110 and introduced into a line 3 and/or a line 4. That is, at least a portion of the effluent of the first reactor 110 is introduced into a first mixing device 120 via the line 3, and the remaining portion of the effluent of the first reactor 110 is decompressed in a first decompression device 131 and then introduced into a water removal device 140 via the line 4. Herein, the effluent of the first reactor 110 may include a catalyst; chlorohydrins; an intermediate product such as glycerol acetates; water; an unreacted polyhydroxy aliphatic hydrocarbon; and/or a chlorination agent. In addition, the chlorination agent is introduced into the first mixing device 120 via the line 2. In the first mixing device 120, the effluent of the first reactor 110 is mixed with the chlorination agent and then recirculated to the first reactor 110.

The first mixing device 120 may be an ejector, an inline mixer, an ultrasonic mixer, or a combination of at least two thereof. When an ejector is used as the first mixing device 120, the effluent of the first reactor 110 may act as a motive fluid and the chlorination agent may act as a suction fluid.

The first decompression device 131 may include a decompression valve.

The additional chlorination agent may include a hydrogen chloride gas or an aqueous hydrochloric acid solution.

The water removal device 140 may operate by performing distillation using a difference between boiling points of constituents of the effluent of the first reactor 110.

In addition, the water removal device 140 may be maintained at an atmospheric pressure or lower, for example, at 10 to 760 mmHg. When the pressure of the water removal device 140 is within this range, a temperature of a downstream effluent (i.e., water-deficient layer) is appropriate, and thus, the amount of a high boiling point material generated is decreased, whereby clogging of the water removal device 140 and pipelines may be prevented. The water removal device 140 may include a vacuum distillation column having a theoretical plate number of 2 to 50 (i.e., a dehydration column 141). When the theoretical plate number of the vacuum distillation column is within this range, the amount of moisture remaining in the water-deficient layer may be minimized. As used herein, the term "theoretical plate number" indicates the number of imaginary regions or plates where two phases, such as gas- and liquid-phases, reach equilibrium, in a separation process using the vacuum distillation column.

The effluent of the first reactor 110 introduced into the water removal device 140 may be discharged when the conversion rate of the polyhydroxy aliphatic hydrocarbon is 30 to 100% and the yield of the chlorohydrins is 30 to 95%, in the first reactor 110. In the effluent of the first reactor 110 introduced into the water removal device 140, when the conversion rate of the polyhydroxy aliphatic hydrocarbon and the yield of chlorohydrins are within the range described above, a reaction rate in the first reactor 110 barely decreases and high water removal effects may be obtained in the water removal device 140. In addition, a high selectivity of the chlorohydrins may be obtained in the first reactor 110. For example, the effluent of the first reactor 110 introduced into the water removal device 140 may include 0 to 90 parts by weight of the polyhydroxy aliphatic hydrocarbon, 5 to 95 parts by weight of the chlorohydrins, and 5 to 12 parts by weight of the intermediate product (e.g., glycerol acetates).

In addition, the effluent of the first reactor 110 introduced into the water removal device 140 may include 10 to 25 parts by weight of the total of the chlorination agent and the additional chlorination agent and 75 to 90 parts by weight of water. When the amounts of the chlorination agent and the water are within the range described above, the effluent of the first reactor 110 may form an azeotropic mixture, and thus, the solubility of the chlorination agent with respect to the water increases so that a loss of the chlorination agent may be minimized.

The effluent of the first reactor 110 introduced into the water removal device 140 via the line 4 is separated into a gas-phase material and other materials (i.e., a liquid-phase material and a solid-phase material) in a dehydration column 141. Thereafter, the gas phase material is condensed in a first condenser 143 and flows into a line 5, and the other materials are distilled in a first reboiler 142 and separated again into a gas-phase material and other materials. Afterwards, the gas-phase material is recirculated to the dehydration column 141 and the other materials are introduced into the second reactor 150 via a line 6. In particular, a material (hereinafter, referred to as a "water-rich layer") that is condensed in the first condenser 143 and flows into the line 5 after being discharged from an upper portion of the dehydration column 141 may include water and the chlorination agent, and a material (hereinafter, referred to as a "water-deficient layer") that does not vaporize in the first reboiler 142 and flows into the line 6 after being discharged from a lower portion of the dehydration column 141 may include an unreacted polyhydroxy aliphatic hydrocarbon, chlorohydrins, and/or the above-described intermediate product. The intermediate product is introduced into the second reactor 150 and acts as a catalyst for the chlorination reaction of Reaction Scheme 1, and thus, the reaction may smoothly occur in the second reactor 150 without further adding a catalyst.

The first reboiler 142 and the first condenser 143 may be maintained at 100 to 200° C. and 0 to 60° C., respectively.

The second reactor 150 may be maintained at 70 to 200° C. When the temperature of the second reactor 150 is within this range, chlorohydrins may be obtained with a high yield by the application of an appropriate level of energy. In addition, the second reactor 150 may be maintained at an atmospheric pressure or above, for example, 1 to 20 atm. When the pressure of the second reactor 150 is within this range, the solubility of the chlorination agent with respect to the contents of the second reactor 150 may be improved. The second reactor 150 may be a CSTR, but is not limited thereto. For example, the second reactor 150 may be a batch reactor, a semi-batch reactor, or a plug flow reactor. In the second reactor 150, chlorohydrins are additionally generated by contacting the above-described intermediate product with an additional chlorination agent that is separately added to the second reactor 150. The retention time of the reactor contents in the second reactor 150 may be from 1 to 3 hours. When the retention time of the reactor contents in the second reactor is within this range, chlorohydrins may be obtained with a high yield within an appropriate time.

The reaction that occurs in the second reactor 150 is the same as or similar to that occurring in the first reactor 110.

After the retention time elapses, an effluent of the second reactor 150 is discharged from the second reactor 150 and introduced into a line 7 and/or a line 9. That is, at least a portion of the effluent of the second reactor 150 is introduced into a second mixing device 160 via the line 7, and the remaining portion of the effluent of the second reactor 150 is decompressed in a second decompression device 132 and then introduced into a first distillation device 170 via the line 9. In this regard, the effluent of the second reactor 150 may include a catalyst; chlorohydrins; an intermediate product such as glycerol acetates; water; an unreacted polyhydroxy aliphatic hydrocarbon; and/or a chlorination agent. The additional chlorination agent is introduced into the second mixing device 160 via a line 8. In the second mixing device 160, the effluent of the second reactor 150 is mixed with the additional chlorination agent, and the resulting mixture is then recirculated to the second reactor 150. The additional chlorination agent may be introduced into the second reactor 150 via other paths, in addition to the line 8.

The second mixing device 160 may be an ejector, an inline mixer, an ultrasonic mixer, or a combination of at least two thereof. When an ejector is used as the second mixing device 160, the effluent of the second reactor 150 may act as a motive fluid and the additional chlorination agent may act as a suction fluid.

The second decompression device 132 may include a decompression valve.

The first distillation device 170 may operate by performing distillation using a difference between boiling points of constituents of the second reactor effluent.

In addition, the first distillation device 170 may be maintained at an atmospheric pressure or below, for example, 10 to 760 mmHg. When the pressure of the first distillation device 170 is within this range, chlorohydrins may be separated with a high efficiency. The first distillation device 170 may include a vacuum distillation column having a theoretical plate number of 2 to 50 (i.e., a separation column 171). When the theoretical plate number of the vacuum distillation column is within this range, chlorohydrins may be separated with a high efficiency.

The effluent of the second reactor 150 introduced into the first distillation device 170 may include 0 to 10 parts by weight of the polyhydroxy aliphatic hydrocarbon, 80 to 98 parts by weight of the chlorohydrins, 0 to 10 parts by weight of the total of the chlorination agent and the additional chlorination agent, and 1 to 20 parts by weight of water. When the amounts of the constituents of the effluent of the second reactor 150 are within the range described above, the reaction is completed and thus the yield of chlorohydrins is maximized.

The effluent of the second reactor 150 that has been introduced into the first distillation device 170 via the line 9 is separated into a gas-phase material and a liquid-phase material in the separation column 171. Thereafter, the gas-phase material is condensed in a second condenser 173 and flows into a line 10, and the liquid-phase material is distilled in a second reboiler 172 and separated again into a gas-phase material and a liquid-phase material. Afterwards, the gas-phase material is recirculated to the separation column 171 and the liquid-phase material is introduced into a stripping device 180 via a line 11. In particular, a material that is condensed in the second condenser 173 and flows into the line 10 after being discharged from an upper portion of the separation column 171 may include chlorohydrins, water and/or the chlorination agent, and a high boiling point material that does not vaporize in the second reboiler 172 and flows into the line 11 after being discharged from a lower portion of the separation column 171 may include an intermediate product, such as glycerol acetate. In this regard, a considerable amount of chlorohydrins may be introduced into the line 11 together with the intermediate product. Herein, the second reboiler 172 and the second condenser 173 may be maintained at a temperature of 100 to 200° C. and 0 to 60° C., respectively.

In the first distillation device 170, a chlorination reaction of the polyhydroxy aliphatic hydrocarbon, i.e., a reaction for producing chlorohydrins, may further occur.

The stripping device 180 separates a low boiling point material, such as chlorohydrins, that is introduced together with the high boiling point material via the line 11 by using steam that is introduced via a line 12. The low boiling point material that is collected by the stripping device 180 flows into a line 13, and the high boiling point material is discharged to the outside via a line 14.

The first distillation device 170 and the stripping device 180 are collectively referred to as a chlorohydrin refiner.

The materials that are introduced into the lines 10 and 13 are collectively referred to as a concentrate of chlorohydrins.

The materials that have been introduced into the lines 5, 10 and 13 may be combined together at a certain location to form a first composition of chlorohydrins.

The first composition of chlorohydrins may include 0 to 10 parts by weight of the polyhydroxy aliphatic hydrocarbon, 60 to 96 parts by weight of the chlorohydrins, 0 to 20 parts by weight of the total of the chlorination agent and the additional chlorination agent, and 0 to 30 parts by weight of water.

When the method of preparing chlorohydrins as described above is used, water as a by-product is removed without a loss of the chlorination agent and/or the catalyst, whereby a reduction in reaction rate may be prevented and the selectivity of chlorohydrins may be increased.

The first composition of chlorohydrins may be used to prepare epichlorohydrin. In this regard, the first composition of chlorohydrins may be diluted with water before being used to prepare epichlorohydrin to form a second composition of chlorohydrins. In particular, referring to FIG. 1, the first composition of chlorohydrins that has been introduced via a line 15 may be mixed with water that has been introduced via a line 16 to form the second composition of chlorohydrins. This process is performed since, when epichlorohydrin is prepared using a high concentration of chlorohydrins, the amounts of by-products increase, and thus, the selectivity of the epichlorohydrin is decreased. In the diluting process, the amount of the water added may be from 100 to 500 parts by weight based on 100 parts by weight of the first composition of chlorohydrins. When the amount of the water added is within this range, the amount of by-products may be reduced by an appropriate amount of water, whereby the yield of the epichlorohydrin may be maximized.

The second composition of chlorohydrins may be used as a reactant for the preparation of epichlorohydrin along with an alkaline agent. The second composition of chlorohydrins may include 0 to 5 parts by weight of the polyhydroxy aliphatic hydrocarbon, 10 to 40 parts by weight of the chlorohydrins, 0 to 5 parts by weight of the total of the chlorination agent and the additional chlorination agent, and 50 to 90 parts by weight of water.

When the amounts of constituents of the second composition of chlorohydrins are within the range described above, the amounts of by-products decrease, and thus, the yield of the epichlorohydrin may be maximized.

In an inline reactor 190, the second composition of chlorohydrins may contact an alkaline agent (e.g., an aqueous sodium hydroxide solution) that has been introduced via a line 17, which causes the following two reactions to occur. That is, during the contact between the second composition of chlorohydrins and the alkaline agent, the pH of a mixture of the second composition of chlorohydrins and the alkaline agent gradually increases as the contact time elapses. Herein, when the pH of the mixture is 7 or below, the catalyst of the second composition of chlorohydrins may react with the alkaline agent to form an alkali metal salt. The formed alkali metal salt may be precipitated and then removed in a second distillation device 200, which will be described below. On the other hand, when the pH of the mixture is greater than 7, the chlorohydrins (e.g., dichloropropanol) of the second composition of chlorohydrins may react with the alkaline agent to form epichlorohydrin. Herein, the inline reactor 190 may be maintained at a temperature of 20 to 100° C. and at a pressure of 1 to 2 atm. When the temperature and pressure of the inline reactor 190 are within this range, the reaction may smoothly progress by the application of an appropriate energy.

In addition, the first composition of chlorohydrins may include the above-described catalyst, and accordingly, the second composition of chlorohydrins may include the catalyst. Consequently, the two reactions may occur in the inline reactor 190: a reaction for forming epichlorohydrin, which is a main product; and a reaction for forming an alkali metal salt by contacting the catalyst with the alkaline agent.

As described above with reference to FIG. 1, the second composition of chlorohydrins is formed by adding water to the first composition of chlorohydrins (i.e., the composition introduced via the line 15) and the alkaline agent is added to the second composition of chlorohydrins; however, the present invention is not limited thereto. Alternatively, the second composition of chlorohydrins may be prepared by directly adding an alkaline agent to the first composition of chlorohydrins to remove the catalyst and adding water to the first composition of chlorohydrins from which the catalyst is removed. That is, in FIG. 1, the dispositions of the lines 16 and 17 may be reversed.

A material including the epichlorohydrin and the alkali metal salt which has been discharged from the inline reactor 190 is introduced into the second distillation device 200 via a line 18.

The second distillation device 200 may operate by performing distillation using a difference between boiling points of constituents of the material including the epichlorohydrin and the alkali metal salt.

In addition, the second distillation device 200 may be maintained at an atmospheric pressure or below, for example, 10 to 760 mmHg. When the pressure of the second distillation device 200 is within this range, epichlorohydrin may be separated with a high efficiency. The second distillation device 200 may include a vacuum distillation column having a theoretical plate number of 2 to 50 (i.e., a second separation column 201). When the theoretical plate number of the vacuum distillation column is within this range, epichlorohydrin may be separated with a high efficiency.

An effluent of the inline reactor 190 that has been introduced into the second distillation device 200 via the line 18 is separated into a gas-phase material and a liquid-phase material. Thereafter, the gas phase material is condensed in a third condenser 203, introduced into a line 19, and then collected, and the liquid-phase material is distilled in a third reboiler 202 to be separated again into a gas-phase material and a liquid-phase material. Afterwards, the gas-phase material is recirculated to the second separation column 201 and the liquid-phase material is discharged to the outside via a line 20. In particular, a material that is condensed in the third condenser 203 and introduced into the line 19 after being discharged from an upper portion of the second separation column 201 may include epichlorohydrin and water, and a high boiling point material that does not vaporize in the third reboiler 202 and is discharged to the outside via the line 20 after being discharged from a lower portion of the second separation column 201 may include an alkali metal salt. Herein, the third reboiler 202 and the third condenser 203 may be maintained at a temperature of 60 to 110° C. and 0 to 60° C., respectively.

In the second distillation device 200, a reaction for producing epichlorohydrin may additionally occur.

One or more embodiments of the present invention will now be described more fully with reference to the following examples. However, these examples are provided only for illustrative purposes and are not intended to limit the scope of the present

EXAMPLE

Preparation of Chlorohydrins and Epichlorohydrin from Glycerol and a Hydrogen Chloride Gas in the Presence of Acetic Acid as a Catalyst Chlorohydrins and epichlorohydrin were prepared by reacting glycerol and a hydrogen chloride gas in the presence of acetic acid as a catalyst by using a manufacturing process as illustrated in FIG. 1. Specifications and operating conditions of devices used in the manufacturing process are as listed below in Table 1.

TABLE 1

|  | Specifications of devices used | Operating conditions | |
|---|---|---|---|
| First reactor | CSTR | 120° C., 4 atm | |
| Two mixing devices | Vacuum ejector | — | |
| Two decompression devices | Decompression valve | 46 mmHg | |
| Water removal device | Vacuum distillation | Dehydration column | Theoretical plate number: 20, Pressure: 23 mmHg |
|  |  | Reboiler | 114° C., 46 mmHg |
|  |  | Condenser | 49° C., 23 mmHg |
| Second reactor | CSTR | 120° C., 4 atm | |
| First distillation device (rear end of water removal device) | Vacuum distillation | Separation column | Theoretical plate number: 20, Pressure: 23 mmHg |
|  |  | Reboiler | 127° C., 46 mmHg |
|  |  | Condenser | 56° C., 23 mmHg |
| Stripping device | Steam stripping | Stripping device | 152 mmHg |
|  |  | Steam | 143° C., 3 atm |
| Inline reactor | Plug flow reactor | 70° C., 1 atm | |
| Second distillation device (rear end of inline reactor) | Vacuum distillation | Separation column | Theoretical plate number: 20 |
|  |  | Reboiler | 104° C., 1 atm |
|  |  | Condenser | 35° C., 1 atm |

In addition, a total flow rate of all materials transferred via each line in the manufacturing process, constituents of the materials, and a flow rate of each constituent were measured and are shown in Table 2 below. The flow rate of each constituent was calculated by measuring the total flow rate of all materials transferred via each line, analyzing a composition ratio of the materials collected from each line by using a gas chromatograph, and multiplying the total flow rate thereof by the composition ratio of the materials.

TABLE 2

| Line No. | Total flow rate (Kg/hr) | Kinds of materials transferred | Flow rate (Kg/hr) |
|---|---|---|---|
| 1 | 315 | Glycerol | 300 |
|  |  | Acetic acid | 15 |
| 2 | 228 | HCl | 228 |
| 3 | 5713 | Monochloropropanediol | 555 |
|  |  | Dichloropropanol | 3444 |
|  |  | Glycerol acetates | 229 |
|  |  | Water | 1083 |
|  |  | Glycerol | 78 |
|  |  | HCl | 269 |
|  |  | Acetic acid | 55 |
| 4 | 543 | Monochloropropanediol | 53 |
|  |  | Dichloropropanol | 327 |
|  |  | Glycerol acetates | 22 |
|  |  | Water | 103 |
|  |  | Glycerol | 7 |
|  |  | HCl | 26 |
|  |  | Acetic acid | 5 |
| 5 | 250 | Dichloropropanol | 116 |
|  |  | Water | 103 |
|  |  | HCl | 26 |
|  |  | Acetic acid | 5 |
| 6 | 293 | Monochloropropanediol | 53 |
|  |  | Dichloropropanol | 211 |
| 7 | 6382 | Glycerol acetates | 22 |
|  |  | Glycerol | 7 |
|  |  | Monochloropropanediol | 268 |
|  |  | Dichloropropanol | 5431 |
|  |  | Glycerol acetates | 443 |
|  |  | Water | 188 |
|  |  | Glycerol | 6 |
|  |  | HCl | 46 |
| 8 | 21 | HCl | 21 |
| 9 | 314 | Monochloropropanediol | 13 |
|  |  | Dichloropropanol | 268 |
|  |  | Glycerol acetates | 22 |
|  |  | Water | 9 |
|  |  | Glycerol | 0 |
|  |  | HCl | 2 |
| 10 | 254 | Dichloropropanol | 243 |
|  |  | Water | 9 |
|  |  | HCl | 2 |
| 11 | 60 | Monochloropropanediol | 13 |
|  |  | Dichloropropanol | 25 |
|  |  | Glycerol acetates | 22 |
|  |  | Glycerol | 0 |
| 12 | 60 | Steam | 60 |
| 13 | 85 | Monochloropropanediol | 2 |
|  |  | Dichloropropanol | 24 |
|  |  | Water | 59 |
| 14 | 35 | Monochloropropanediol | 11 |
|  |  | Dichloropropanol | 1 |

TABLE 2-continued

| Line No. | Total flow rate (Kg/hr) | Kinds of materials transferred | Flow rate (Kg/hr) |
|---|---|---|---|
|  |  | Glycerol acetates | 22 |
|  |  | Water | 1 |
|  |  | Glycerol | 0 |
| 15 | 589 | Monochloropropanediol | 2 |
|  |  | Dichloropropanol | 383 |
|  |  | Water | 171 |
|  |  | Glycerol | 0 |
|  |  | HCl | 28 |
|  |  | Acetic acid | 5 |
| 16 | 2000 | Water | 2000 |
| 17 | 640 | NaOH | 160 |
|  |  | Water | 480 |
| 18 | 3229 | Dichloropropanol | 8 |
|  |  | Epichlorohydrin | 268 |
|  |  | Water | 2718 |
|  |  | Glycerol | 3 |
|  |  | Sodium acetate | 7 |
|  |  | NaCl | 215 |
|  |  | NaOH | 10 |
| 19 | 274 | Dichloropropanol | 0 |
|  |  | Epichlorohydrin | 272 |
|  |  | Water | 2 |
| 20 | 2955 | Water | 2718 |
|  |  | Glycerol | 4 |
|  |  | Sodium acetate | 7 |
|  |  | NaCl | 219 |
|  |  | NaOH | 7 |

Evaluation Example

While the reaction progressed, samples were respectively collected from lines 4 and 15 at intervals of 5 minutes, and constituents of each sample and the amounts of the constituents were analyzed by using a gas chromatography. The conversion rate of glycerol, the yield of monochloropropanediol, the yield of dichloropropanol, the selectivity of monochloropropanediol, and the selectivity of dichloropropanol were calculated using data obtained after reaching a steady state among the analysis data, according to Equations 1 through 5 above, and the calculation results are shown in Table 3 below.

TABLE 3

|  | Sample collection location | |
|---|---|---|
|  | Line 4 | Line 15 |
| Conversion rate of glycerol (%) | 97.5 | 100 |
| Yield of monochloropropanediol (%) | 14.6 | 0.6 |
| Yield of dichloropropanol (%) | 77.9 | 94.2 |
| Yield of chlorohydrins*[1] (%) | 92.5 | 94.8 |
| Selectivity of monochloropropanediol (%) | 14.6 | 0.6 |
| Selectivity of dichloropropanol (%) | 77.9 | 94.2 |
| Selectivity of chlorohydrins*[2] (%) | 92.5 | 94.8 |

*[1]Yield of monochloropropanediol + yield of dichloropropanol
*[2]Selectivity of monochloropropanediol + selectivity of dichloropropanol Referring to Table 3, the yield (i.e., 94.8%) and selectivity (i.e., 94.8%) of chlorohydrins are high in the samples collected from line 15. In addition, the yield and selectivity of dichloropropanol are much higher than those of monochloropropanediol.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of preparing chlorohydrins by reacting polyhydroxy aliphatic hydrocarbon with a chlorination agent in the presence of a catalyst, the method comprising at least one combination of a series of unit operations comprising a plurality of reaction steps and a water removal step in the following stated order:
    a first reaction step of reacting the polyhydroxy aliphatic hydrocarbon with the chlorination agent;
    a water removal step of removing water as a by-product from a reaction mixture discharged from the first reaction step; and
    a second reaction step of reacting at least one constituent of the dehydrated reaction mixture with at least one of the chlorination agent and an additional chlorination agent,
    wherein the method further comprises purifying a reaction mixture discharged from a final reaction step of the plurality of reaction steps to obtain a concentrate of chlorohydrins,
    wherein the catalyst comprises at least one selected from the group consisting of an organic acid catalyst, a carboxylic acid-based catalyst, a nitrile-based catalyst, and a solid catalyst,
    wherein an effluent of the first reactor introduced into the water removal step comprises the chlorination agent and water at a ratio of 10 to 25 parts by weight of the total of the chlorination agent and the additional chlorination agent and 75 to 90 parts by weight of water so that the effluent of the first reactor introduced into the water removal step forms an azeotropic mixture.

2. The method of claim 1, further comprising mixing at least a portion of a reaction mixture discharged from at least one reaction steps from among the plurality of reaction steps, with an additional chlorination agent and then recirculating the resultant mixture to the reaction step from which the reaction mixture was discharged.

3. A method of preparing chlorohydrins, the method comprising:
    introducing polyhydroxy aliphatic hydrocarbon, a catalyst, and a chlorination agent into a first reactor maintained at a temperature of 50 to 200° C.;
    discharging from the first reactor an effluent of the first reactor comprising water as a by-product;
    introducing at least a portion of the effluent of the first reactor into a water removal device;
    introducing the effluent of the first reactor from which water is removed, and an additional chlorination agent into a second reactor maintained at a temperature of 80 to 200° C.; and
    introducing at least a portion of an effluent of the second reactor into a device for purifying chlorohydrins to obtain a concentrate of chlorohydrins,
    wherein the catalyst comprises at least one selected from the group consisting of an organic acid catalyst, a carboxylic acid-based catalyst, a nitrile-based catalyst, and a solid catalyst,
    wherein the effluent of the first reactor introduced into the water removal device comprises the chlorination agent and water at a ratio of 10 to 25 parts by weight of the total of the chlorination agent and the additional chlorination agent and 75 to 90 parts by weight of water so that the effluent of the first reactor introduced into the water removal device forms an azeotropic mixture.

4. The method of claim 3, further comprising at least one of a step of introducing at least a portion of the effluent of the first reactor with an additional chlorination agent into a first mixer, mixing them together, and recirculating the resulting mixture to the first reactor; and a step of introducing at least a portion of the effluent of the second reactor with an additional chlorination agent into a second mixer, mixing them together, and recirculating the resulting mixture to the second reactor.

5. The method of claim 1, wherein the polyhydroxy aliphatic hydrocarbon is a $C_2$-$C_{20}$ compound having at least two hydroxyl groups bonded to different carbon atoms.

6. The method of claim 5, wherein the polyhydroxy aliphatic hydrocarbon is selected from the group consisting of 1,2-ethanediol, 1,2-propanediol, 1,3-propanediol, 3-chloro-1,2-propanediol, 2-chloro-1,3-propanediol, glycerol, 1,2,4-butanetriol, 1,4-butanediol, esters of these compounds and mixtures thereof.

7. The method of claim 1, wherein chlorohydrins of the concentrate of chlorohydrins are compounds having at least one hydroxyl group and at least one chlorine atom which are bonded to different carbon atoms.

8. The method of claim 7, wherein the chlorohydrins comprise at least one compound selected from the group consisting of 3-chloro-1,2-propanediol, 2-chloro-1,3-propanediol, 1,3-dichloropropane-2-ol, and 2,3-dichloropropane-1-ol.

9. The method of claim 3, wherein a reaction product of the catalyst and the polyhydroxy aliphatic hydrocarbon is produced as an intermediate product in the first reactor, and the intermediate product acts as a catalyst in a chlorination reaction of the polyhydroxy aliphatic hydrocarbon.

10. The method of claim 9, wherein the polyhydroxy aliphatic hydrocarbon is glycerol, the catalyst is acetic acid, and the intermediate product is glycerol acetate.

11. The method of claim 1, wherein the chlorination agent and the additional chlorination agent comprise a hydrogen chloride gas or an aqueous hydrochloric acid solution.

12. The method of claim 3, wherein the effluent of the first reactor introduced into the water removal device is discharged when a conversion rate of the polyhydroxy aliphatic hydrocarbon is from 30 to 100% and a yield of chlorohydrins is 30 to 95%, in the first reactor.

13. The method of claim 9, wherein the effluent of the first reactor introduced into the water removal device comprises 0 to 90 parts by weight of the polyhydroxy aliphatic hydrocarbon; 5 to 95 parts by weight of the chlorohydrins; and 5 to 12 parts by weight of the intermediate product.

14. The method of claim 3, wherein the device for purifying chlorohydrins comprises a distillation device.

15. The method of claim 14, wherein the device for purifying chlorohydrins further comprises a stripping device at a rear end of the distillation device.

16. The method of claim 3, wherein a retention time of the reactor contents in the first reactor is from 20 minutes to 1 hour, and a retention time of the reactor contents in the second reactor is from 1 to 3 hours.

17. The method of claim 3, wherein the water removal device operates by performing distillation using a difference between boiling points of constituents of the effluent of the first reactor.

18. The method of claim 3, wherein the first and second reactors are maintained at an atmospheric pressure or higher, and the water removal device is maintained at an atmospheric pressure or lower.

19. The method of claim 18, wherein the first and second reactors are maintained at 1 to 20 atm, and the water removal device is maintained at 10 to 760 mmHg.

20. The method of claim 19, wherein the water removal device comprises a vacuum distillation column having a theoretical plate number of 2 to 50.

21. The method of claim 18, wherein the effluent of the first reactor is decompressed in a decompression device and then introduced into the water removal device.

22. The method of claim 21, wherein the decompression device comprises a decompression valve.

23. The method of claim 3, wherein the first and second reactors are each independently a continuous stirred tank reactor, a batch reactor, a semi-batch reactor, or a plug flow reactor.

24. The method of claim 3, wherein the effluent of the first reactor introduced into the water removal device is separated into a water-rich layer and a water-deficient layer.

25. The method of claim 3, wherein a portion of the effluent of the second reactor which is introduced into the device for purifying chlorohydrins comprises 0 to 10 parts by weight of the polyhydroxy aliphatic hydrocarbon, 80 to 98 parts by weight of the chlorohydrins, 0 to 10 parts by weight of the total of the chlorination agent and the additional chlorination agent, and 1 to 20 parts by weight of water.

26. The method of claim 3, wherein the polyhydroxy aliphatic hydrocarbon is a $C_2$-$C_{20}$ compound having at least two hydroxyl groups bonded to different carbon atoms.

27. The method of claim 3, wherein chlorohydrins of the concentrate of chlorohydrins are compounds having at least one hydroxyl group and at least one chlorine atom which are bonded to different carbon atoms.

28. The method of claim 27, wherein the chlorohydrins comprise at least one compound selected from the group consisting of 3-chloro-1,2-propanediol, 2-chloro-1,3-propanediol, 1,3-dichloropropane-2-ol, and 2,3-dichloropropane-1-ol.

29. The method of claim 4, wherein the chlorination agent and the additional chlorination agent comprise a hydrogen chloride gas or an aqueous hydrochloric acid solution.

* * * * *